(12) United States Patent
Schleich et al.

(10) Patent No.: US 9,180,295 B2
(45) Date of Patent: Nov. 10, 2015

(54) TONOTOPIC IMPLANT STIMULATION

(75) Inventors: Peter Schleich, Vill (AT); Peter Nopp, Birgitz (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 695 days.

(21) Appl. No.: 12/427,933

(22) Filed: Apr. 22, 2009

(65) Prior Publication Data

US 2009/0264961 A1 Oct. 22, 2009

Related U.S. Application Data

(60) Provisional application No. 61/046,832, filed on Apr. 22, 2008.

(51) Int. Cl.
*A61N 1/00* (2006.01)
*H04R 25/00* (2006.01)
(Continued)

(52) U.S. Cl.
CPC ............. *A61N 1/36032* (2013.01); *A61F 11/04* (2013.01); *A61N 1/0541* (2013.01); *A61N 1/08* (2013.01);
(Continued)

(58) Field of Classification Search
CPC ... A61N 1/36032; A61N 1/0541; A61N 1/08; H04R 25/552; H04R 2225/41; H04R 2225/43; H04R 25/353; H04R 25/606; G02C 11/06; A61F 11/04
USPC ........................ 607/55, 56, 57, 137; 381/23.1, 381/312–317, 321, 320; 12/55, 56, 57, 137
See application file for complete search history.

(56) References Cited

U.S. PATENT DOCUMENTS

| | | | |
|---|---|---|---|
| 4,515,158 A | 5/1985 | Patrick et al. | 128/419 R |
| 5,434,924 A * | 7/1995 | Jampolsky | 381/23.1 |

(Continued)

FOREIGN PATENT DOCUMENTS

| | | | | |
|---|---|---|---|---|
| EP | 1338301 A1 | 8/2003 | | A61N 1/36 |
| WO | WO 99/49815 | 10/1999 | | A61F 2/18 |

(Continued)

OTHER PUBLICATIONS

McKay, Colette, et al, "The effect of rate of stimulation on perception of spectral shape by cochlear implantees", *Journal of Acoustical Society of America*, AIP/Acoustical Society of America, Melville, NY, US, vol. 118; No. 1; Jan. 1, 2005, pp. 386-392; XP012073185; ISSN: 001-4966.

(Continued)

*Primary Examiner* — Niketa Patel
*Assistant Examiner* — Lindsey G Hankins
(74) *Attorney, Agent, or Firm* — Sunstein Kann Murphy & Timbers LLP (57) ABSTRACT

Electrode stimulation signals are generated for an implanted electrode array. An acoustic audio signal is processed with a bank of filters that are each associated with a band of audio frequencies, and a set of band pass signals is generated with each band pass signal corresponding to the band of frequencies associated with one of the filters. Stimulation information is extracted from the band pass signals to generate a set of stimulation event signals defining electrode stimulation signals. Then the stimulation event signals are weighted with a weighted matrix of stimulation amplitudes reflecting patient-specific perceptual characteristics to produce a set of electrode stimulation signals for electrodes in the implanted electrode array.

26 Claims, 9 Drawing Sheets

(51) Int. Cl.
*A61N 1/36* (2006.01)
*A61F 11/04* (2006.01)
*A61N 1/08* (2006.01)
*A61N 1/05* (2006.01)

(52) U.S. Cl.
CPC ............. *H04R 25/353* (2013.01); *H04R 25/552* (2013.01); *H04R 2225/41* (2013.01); *H04R 2225/43* (2013.01)

(56) References Cited

U.S. PATENT DOCUMENTS

| | | | |
|---|---|---|---|
| 7,204,417 B2 | 5/2003 | Hillard | 221/25 |
| 6,584,525 B1 | 6/2003 | Klingman | 701/118 |
| 6,778,858 B1 | 8/2004 | Peeters | 607/57 |
| 7,072,717 B1 | 7/2006 | Wolf et al. | 607/57 |
| 7,149,583 B1 | 12/2006 | Litvak | 607/57 |
| 7,209,789 B2 | 4/2007 | Zierhofer | 607/57 |
| 7,225,027 B2 | 5/2007 | Zeng | 607/57 |
| 7,251,530 B1 | 7/2007 | Overstreet et al. | 607/55 |
| 7,292,892 B2 | 11/2007 | Litvak et al. | 607/57 |
| 7,310,558 B2 | 12/2007 | Van Hoesel | 607/57 |
| 7,421,298 B2 | 9/2008 | Daly et al. | 607/57 |
| 2001/0031909 A1 | 10/2001 | Faltys et al. | 600/25 |
| 2004/0082985 A1 | 4/2004 | Faltys et al. | 607/116 |
| 2004/0252852 A1* | 12/2004 | Taenzer | 381/119 |
| 2005/0107843 A1 | 5/2005 | McDermott et al. | 607/57 |
| 2005/0203589 A1 | 9/2005 | Zierhofer | 607/57 |
| 2006/0052841 A1 | 3/2006 | Daly et al. | 607/57 |
| 2006/0100672 A1* | 5/2006 | Litvak | 607/57 |
| 2006/0265061 A1 | 11/2006 | Kwon et al. | 623/10 |
| 2007/0156202 A1 | 7/2007 | Zierhofer | 607/57 |
| 2007/0225776 A1 | 9/2007 | Fritsch et al. | 607/57 |
| 2008/0172108 A1 | 7/2008 | Zierhofer et al. | 607/57 |
| 2009/0012580 A1 | 1/2009 | Arnoldner et al. | 607/57 |
| 2010/0198300 A1 | 8/2010 | Smith | 607/57 |
| 2010/0198301 A1 | 8/2010 | Smith | 607/57 |

FOREIGN PATENT DOCUMENTS

| | | | |
|---|---|---|---|
| WO | WO 01/19135 A1 | 3/2001 | H04R 25/00 |
| WO | WO 01/19304 A1 | 3/2001 | |
| WO | WO 2005/113064 A | 12/2005 | |
| WO | WO 2006/119069 | 11/2006 | |

OTHER PUBLICATIONS

Secker-Walker, H., et al, "Time-domain analysis of auditory-nerve-fiber firing rates", *J. Acoust. Soc. Am.* 88(3), pp. 1427-1436 (1990).
Wilson, B.S., et al, "Temporal Representations With Cochlear Implants", *Am. J. Otology*, vol. 18, No. 6 (Suppl), S30-S34, (1997).
Wilson, B.S., et al, "Comparative Studies of Speech Processing Strategies for Cochlear Implants", *Laryngoscope* (1998); pp. 1069-1077.
Zeng, F., et al, "Cochlear Implants: System Design, Integration, and Evaluation", *IEEE Reviews in Biomedical Engineering*, vol. 1, 2008, pp. 115-142.
Ziese, M., et al, "Speech Understanding with the CIS and the n-of-m Strategy in the MED-EL COMBI 40+ System", *ORL* 2000:62:321-329.
European Patent Office, International Search Report dated Nov. 16, 2005, PCT/IB2005/002349.
European Patent Office, International Search Report dated Jan. 27, 2009, PCT/US2008/079923.
European Patent Office, International Search Report dated Sep. 3, 2009, PCT/IB2009/005813.

* cited by examiner

*FIG. 1*

PRIOR ART

TONOTOPIC IMPLANT STIMULATION

This application claims priority from U.S. Provisional Patent Application 61/046,832, filed Apr. 22, 2008, which is incorporated herein by reference.

FIELD OF THE INVENTION

The present invention relates to cochlear implants, and specifically to the signal processing used therein.

BACKGROUND ART

Figure 1:
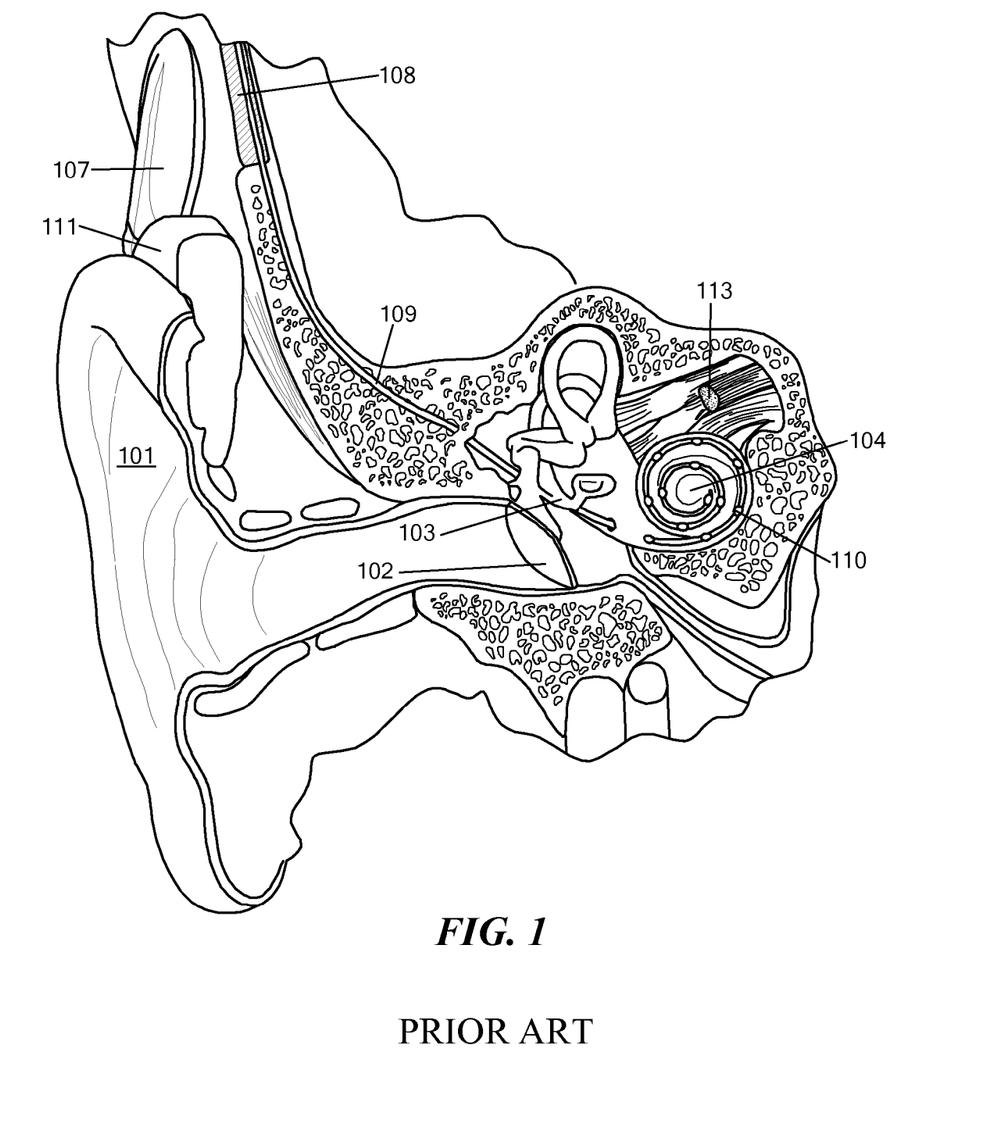
FIG. 1 illustrates a sectional view of an ear connected to a cochlear implant system according to an embodiment of the present invention.

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission by an external transmitter coil 107 into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrodes on its surface that provide selective stimulation of the cochlea 104.

In cochlear implants today, a relatively small number of electrodes are each associated with relatively broad frequency bands, with each electrode addressing a group of neurons through a stimulation pulse the charge of which is derived from the instantaneous amplitude of the envelope within that frequency band. In some coding strategies, stimulation pulses are applied at constant rate across all electrodes, whereas in other coding strategies, stimulation pulses are applied at an electrode-specific rate.

Various signal processing schemes can be implemented to produce the electrical stimulation signals. Signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, and compressed analog (CA) signal processing. For example, in the CIS approach, signal processing for the speech processor involves the following steps:

(1) splitting up of the audio frequency range into spectral bands by means of a filter bank,
(2) envelope detection of each filter output signal,
(3) instantaneous nonlinear compression of the envelope signal (map law).

According to the tonotopic organization of the cochlea, each stimulation electrode in the scala tympani is associated with a band pass filter of the external filter bank. For stimulation, symmetrical biphasic current pulses are applied. The amplitudes of the stimulation pulses are directly obtained from the compressed envelope signals. These signals are sampled sequentially, and the stimulation pulses are applied in a strictly non-overlapping sequence. Thus, as a typical CIS-feature, only one stimulation channel is active at one time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be chosen arbitrarily short, because the shorter the pulses, the higher the current amplitudes have to be to elicit action potentials in neurons, and current amplitudes are limited for various practical reasons. For an overall stimulation rate of 18 kpps, the phase duration is 27 µs, which is near the lower limit. Each output of the CIS band pass filters can roughly be regarded as a sinusoid at the center frequency of the band pass filter which is modulated by the envelope signal. This is due to the quality factor ($Q \approx 3$) of the filters. In case of a voiced speech segment, this envelope is approximately periodic, and the repetition rate is equal to the pitch frequency.

In the existing CIS-strategy, only the envelope signals are used for further processing, i.e., they contain the entire stimulation information. For each channel, the envelope is represented as a sequence of biphasic pulses at a constant repetition rate. A characteristic feature of CIS is that this repetition rate (typically 1.5 kpps) is equal for all channels and there is no relation to the center frequencies of the individual channels. It is intended that the repetition rate is not a temporal cue for the patient, i.e., it should be sufficiently high, so that the patient does not perceive tones with a frequency equal to the repetition rate. The repetition rate is usually chosen at greater than twice the bandwidth of the envelope signals (Nyquist theorem).

Figure 2:
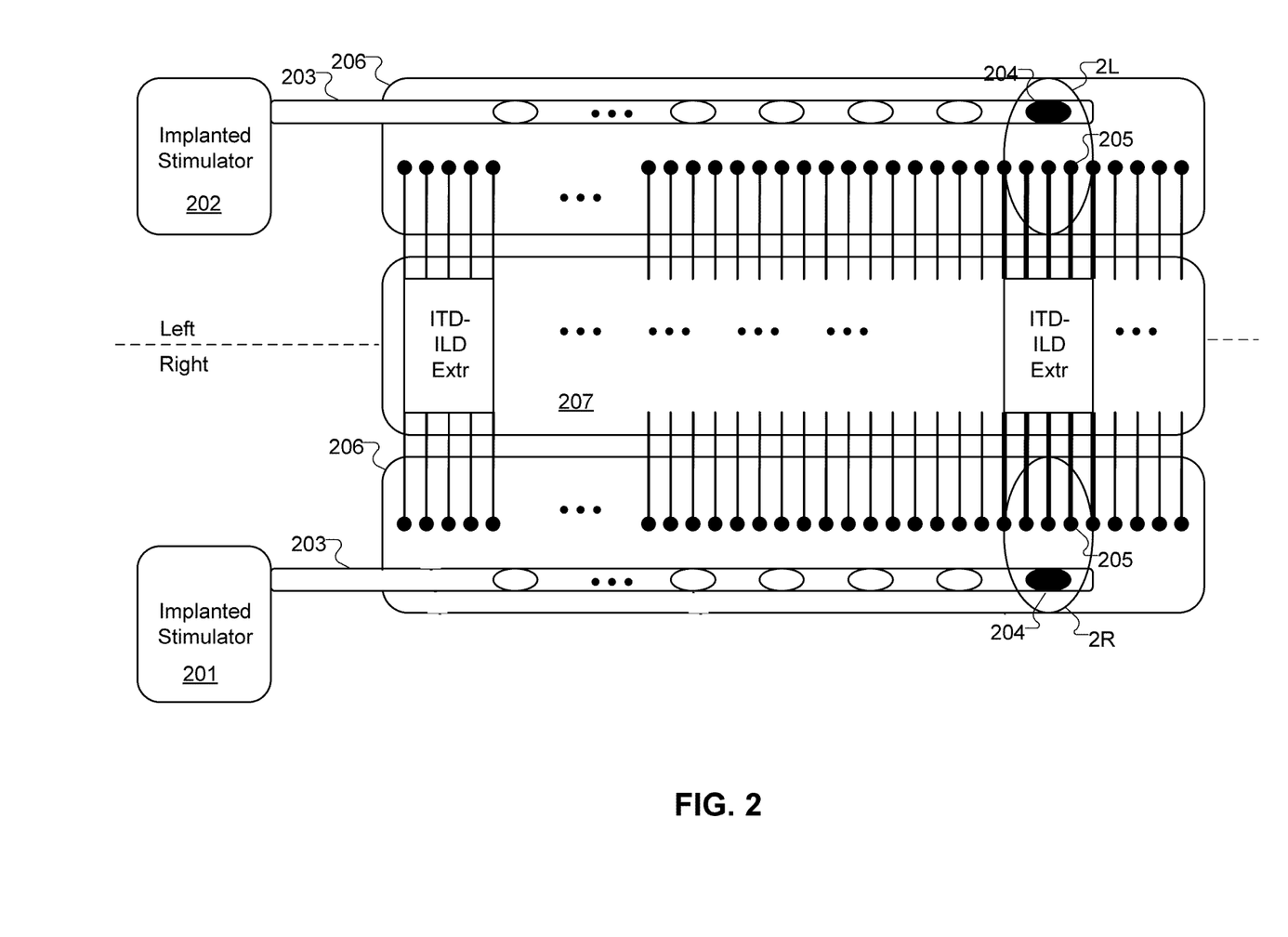
FIG. 2 illustrates an example of bilateral cochlear implants in a patient having interaurally matched electrode insertions as well as matched tonotopicity.

In some patients, cochlear implant systems are implanted bilaterally with two separate independent systems, one on each side. FIG. 2 shows an example of a bilateral cochlear implant in patient having a right-side implanted stimulator 201 and an independent left-side implanted stimulator 202. Each implanted stimulator has a corresponding electrode array 203 which penetrates the cochlea 206 to place a linear array of electrode contacts 204 adjacent to audio neural tissue 205 in the cochlea. The implanted stimulator (201 on the right-side, 202 on the left-side) provides electrode-specific stimulation signals to the electrode contacts 204 which provide a corresponding electrical stimulus signal to the near adjacent audio neural tissue 205, which in the aggregate are perceived by the brain 207 as sound. In the example shown in FIG. 2, the system is shown in an idealized optimal alignment in which the insertion of the corresponding left and right electrode arrays 203 results in a matching left-right alignment of electrode contacts 204 and neural tissue 205 so that corresponding electrode contacts 204 on both sides align with and stimulate corresponding neural tissue on each side, as shown by comparing regions 2R and 2L.

To localize or track sounds in three dimensional listening situations, the brain 207 extracts from the stimulation signals acoustic information which includes interaural time delays (ITD) and interaural level differences (ILD). Normal hearing persons are believed to extract ITDs and ILDs across ears within relatively narrow frequency bands, and in contrast to CI users, normal hearing persons have a 'natural' allocation of frequencies to specific locations within the cochlea and further on to specific neural populations, i.e. ITDs or ILDs presented within a certain frequency band can be decoded by higher neural structures. In CI users the allocation of frequency bands to certain neural populations is defined, e.g., by the position of the electrodes, the amount of neural survival in certain regions, as well as the filter bank used.

Figure 3:
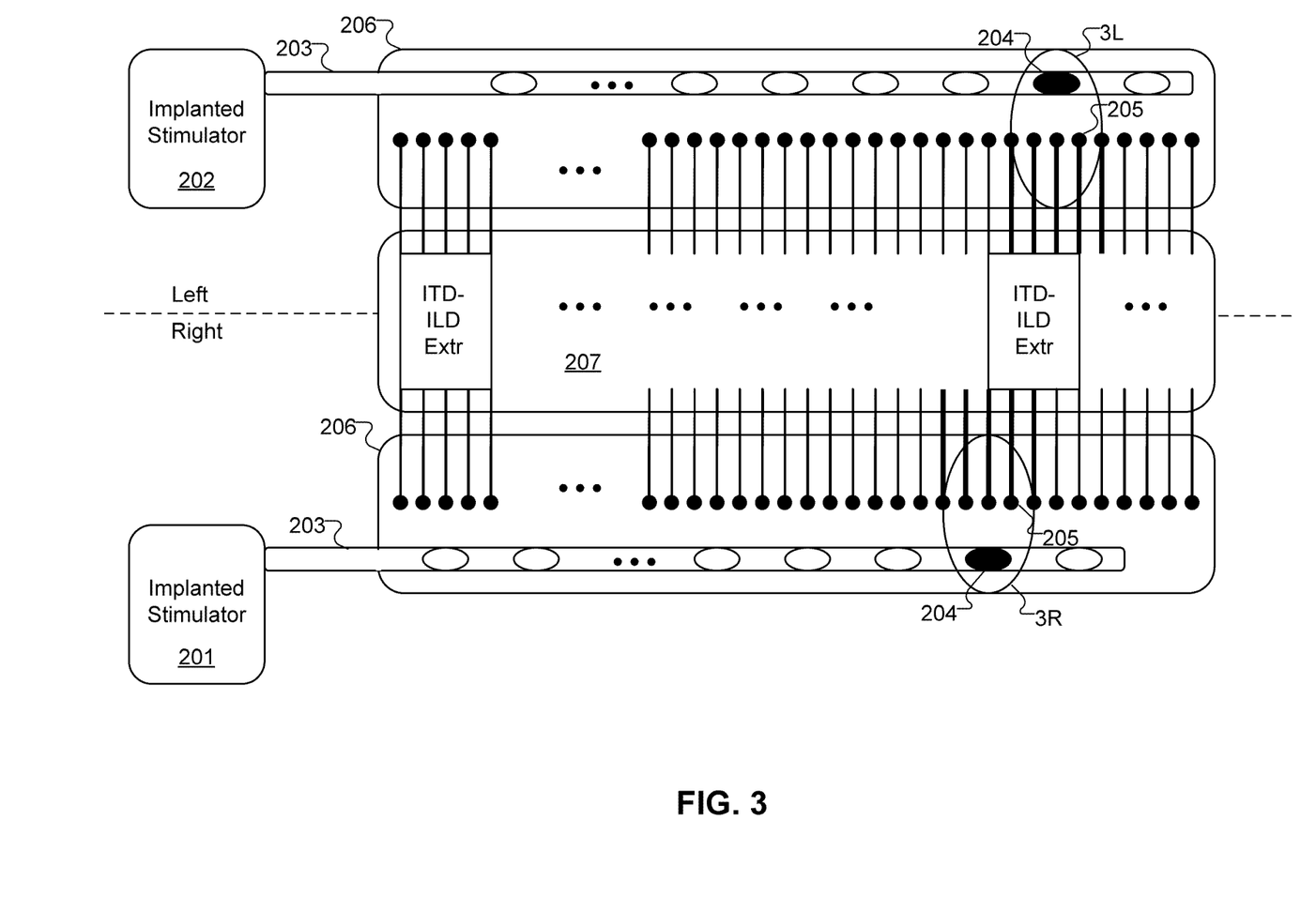
FIG. 3 illustrates an example of bilateral cochlear implants in a patient having interaurally mismatched electrode insertions.

As described above, in current CI systems an acoustic signal is typically decomposed into a set of band pass signals. Each of these band pass signals has a different group delay ranging from some 100 µs for high frequency filters to several milliseconds for low frequency filters. On the other hand, typical acoustic ITDs range from about −700 µs to +700 µs. If the nerve populations stimulated by interaural electrode pairs are matched as shown in FIG. 2 (compare regions 2R and 2L), then the evaluation of ITDs and ILDs is permitted. However, in a typical bilateral CI system, the insertion depths between the right ear and the left ear are slightly different because of effects which cannot be controlled by the surgeon (e.g. different insertion frictions, different degrees of ossifications, different cochleostomies, etc.). Compensation for such an interaural mismatch of neural populations by stimulation with a corresponding electrode pair on either the left or the right CI (see FIG. 3 and compare regions 3R and 3L) would result in nerve signals carrying information from different band pass signals and therefore being affected by largely different group delays—ITD as well as ILD extraction would be hindered. Filter bank settings, filter-to-electrode assignment, and physical electrode positions currently are not generally adapted to patient specific needs.

Existing CI signal processing strategies do not take into account interaural differences in electrode placement and excited neural populations, or patient-specific tonotopicity of electrode contacts. Typically, patient-specific fitting of coding strategies for bilateral CI users involves independently fitting each individual system and then balancing the overall loudness of both systems together. Specifically, tonotopic mismatch between electrodes and assigned band pass filters is addressed by changing filter boundaries of the analysis filter bank. Cochlear implant fitting procedures addressing tonotopicity have been described previously, e.g. U.S. Pat. No. 7,292,892 by Litvak U.S. Pat. No. 7,103,417 by Segel; and U.S. Pat. No. 7,251,530 by Overstreet; all of which are incorporated herein by reference. All these methods have in common the generation of a user-specific frequency map of the possibly sub-optimal analysis filter bank.

Existing CI signal processing does not address mismatch of filter-bank analysis and tonotopic pitch perception by stimulation of single electrodes. In particular, sound coding techniques which extract timing information from the acoustic signal to determine the timing of stimulation pulses (e.g. U.S. Pat. No. 7,209,789 by Zierhofer; U.S. Pat. No. 7,072,717 by Wolf, U.S. Pat. No. 7,149,583 by Litvak; U.S. Pat. No. 7,225,027 by Zeng; and U.S. Pat. No. 7,310,558 by van Hoesel; all of which are incorporated herein by reference) might suffer from a tonotopic mismatch between sides in bilateral implant users. U.S. Patent Publication 20090012580 (which is incorporated herein by reference) describes speech processing and electrode stimulation strategies that relate stimulus intensity to pitch perception.

SUMMARY OF THE INVENTION

Embodiments of the present invention are directed to generating electrode stimulation signals for an implanted electrode array. An acoustic audio signal is processed with a bank of filters that are each associated with a band of audio frequencies, and a set of band pass signals is generated with each band pass signal corresponding to the band of frequencies associated with one of the filters. Stimulation information is extracted from the band pass signals to generate a set of stimulation event signals defining electrode stimulation signals. Then the stimulation event signals are weighted with a weighting matrix reflecting patient-specific perceptual characteristics to produce a set of electrode stimulation signals for electrodes in the implanted electrode array.

DETAILED DESCRIPTION OF SPECIFIC EMBODIMENTS

Most existing CI signal processing strategies do not enable bilateral CI users to make use of ITDs to localize sound sources or follow conversations in three dimensional listening environments. However, some existing coding strategies that encode the temporal fine structure of sound signals would seem to have the potential to provide bilateral CI users with appropriate representations of band specific ITDs. Current fine structure coding strategies such as CSSS are usually based on time domain filters, which possess certain group delays that are mainly defined by the center frequency of the associated band pass. Typically, each filter band is associated with a specific electrode contact, but in bilateral CI patients, corresponding electrodes may not necessarily address matched nerve populations. This results in tonotopic and temporal mismatch of bilateral information streams.

The tonotopic mismatch between filter bank and electrode positions could be resolved in existing CI systems by changing center frequencies and boundaries of the band pass filters. In a bilateral CI user, though, this introduces an additional unintended cue. Although electrodes might be correctly perceived tonotopically, filter bands with different group delays have to be used on both sides. Thus ITD analysis is not possible, i.e. different interaural bands contain different ITD information.

Embodiments of the present invention reduce perceptual mismatch of interaural electrode pairs, for example, by applying simultaneous stimulation to a group of electrodes. Stimulation sites can also be tonotopically matched on a subjective scale to the analysis filter bank and/or separate stimulation sites. Rather than assigning the band pass output to an electrical stimulus of specific electrodes, instead a weighted sum of stimuli is applied to a set of electrodes.

Figure 4:
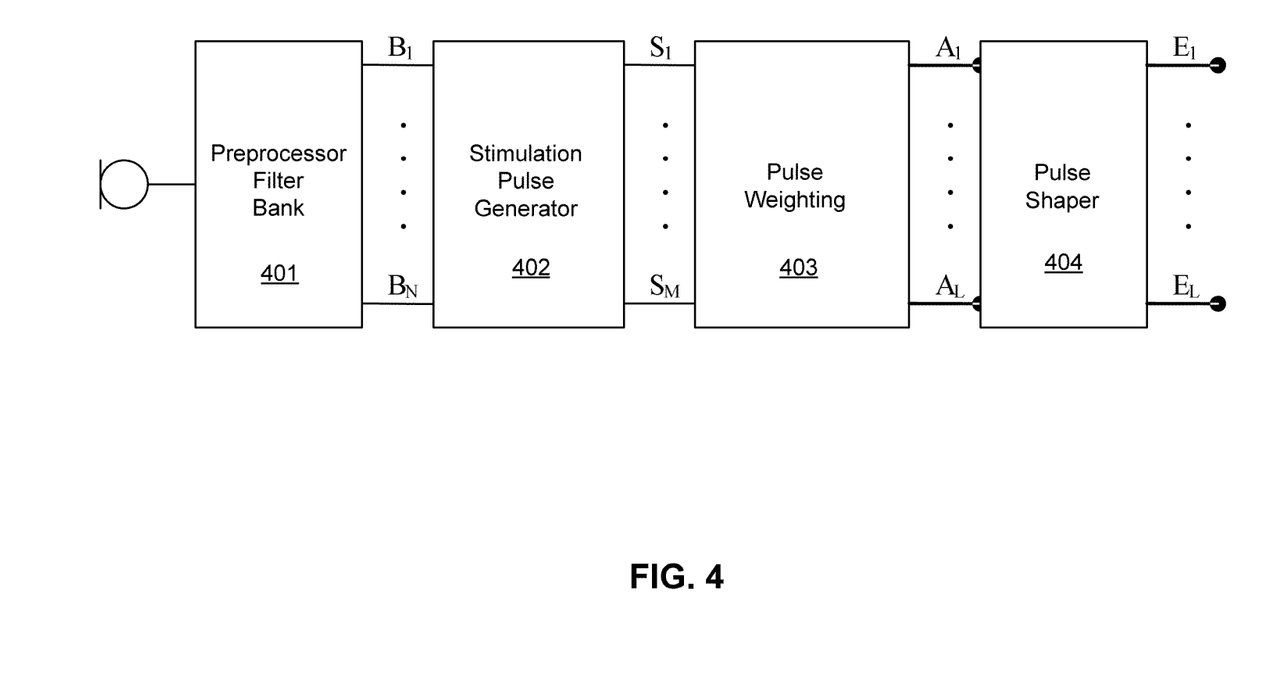
FIG. 4 illustrates a block diagram of a specific embodiment of the present invention.

FIG. 4 shows an example of a specific embodiment that uses an additional processing stage for assigning N band pass signals containing stimulation timing and amplitude information to L stimulation electrodes. Preprocessor Filter Bank 401 pre-processes an initial acoustic audio signal, e.g., automatic gain control, noise reduction, etc. Each band pass filter in the Preprocessor Filter Bank 401 is associated with a specific band of audio frequencies so that the acoustic audio signal is filtered into some N signals, $B_1$ to $B_N$ where each signal corresponds to the band of frequencies for one of the band pass filters. The band pass signals are input to Stimulation Pulse Generator 402 which extracts signal specific stimulation information—e.g., envelope information, phase information, timing of requested stimulation events, etc.—to form a set of M stimulation event signals $S_1$ to $S_M$, which represent electrode specific stimulation signals. In previous conventional CI systems, the $S_1$ to $S_M$ stimulation event signals are mapped to sequential or simultaneous patient specific electrical stimulation signals applied to some L stimulation electrodes, but the system shown in FIG. 4 includes an additional processing block, the Pulse Weighting 403, which weights each stimulation event signal $S_1$ to $S_M$ with a weighted matrix of stimulation amplitudes that reflect patient-specific perceptual characteristics to produce a set of electrode stimulation signals $A_1$ to $A_L$. Pulse Shaper 404 then develops the set of electrode stimulation signals $A_1$ to $A_L$ into a set of output electrode pulses $E_1$ to $E_L$ to the electrodes in the implanted electrode array which stimulate the adjacent nerve tissue. Whenever one of the stimulation event signals $S_1$ to $S_M$ requests a stimulation event, the respective number of electrodes is activated with a set of output electrode pulses $E_1$ to $E_L$.

More specifically, Pulse Weighting 403 may define the weighting of electrodes per band pass signal S by:

$$\vec{A}(t) = W \cdot \vec{S}(t)$$

where at each time instance, S(t) is a vector $S_1(t)$ to $S_M(t)$:

$$S^{\vec{w}} = \begin{pmatrix} S_1(t) \\ S_2(t) \\ S_3(t) \\ \ldots \\ \ldots \\ \ldots \\ \ldots \\ S_M(t) \end{pmatrix}$$

W is a L×M weighting-matrix:

$$W = \begin{pmatrix} 0.8 & 0.2 & 0 & \ldots & \ldots & 0 & 0 & 0 \\ 0.2 & 0.7 & 0.1 & \ldots & \ldots & 0 & 0 & 0 \\ 0 & 0.1 & 0.9 & \ldots & \ldots & 0 & 0 & 0 \\ \ldots & \ldots & \ldots & \ldots & \ldots & \ldots & \ldots & \ldots \\ \ldots & \ldots & \ldots & \ldots & \ldots & \ldots & \ldots & \ldots \\ 0 & 0 & 0 & \ldots & \ldots & 0 & 0.2 & 1 \end{pmatrix}$$

and A(t) is a vector $A_1(t)$ to $A_L(t)$ of normalized stimulation amplitudes:

$$A^{\vec{w}} = \begin{pmatrix} A_1(t) \\ A_2(t) \\ A_3(t) \\ \ldots \\ \ldots \\ A_L(t) \end{pmatrix}$$

Figure 5:
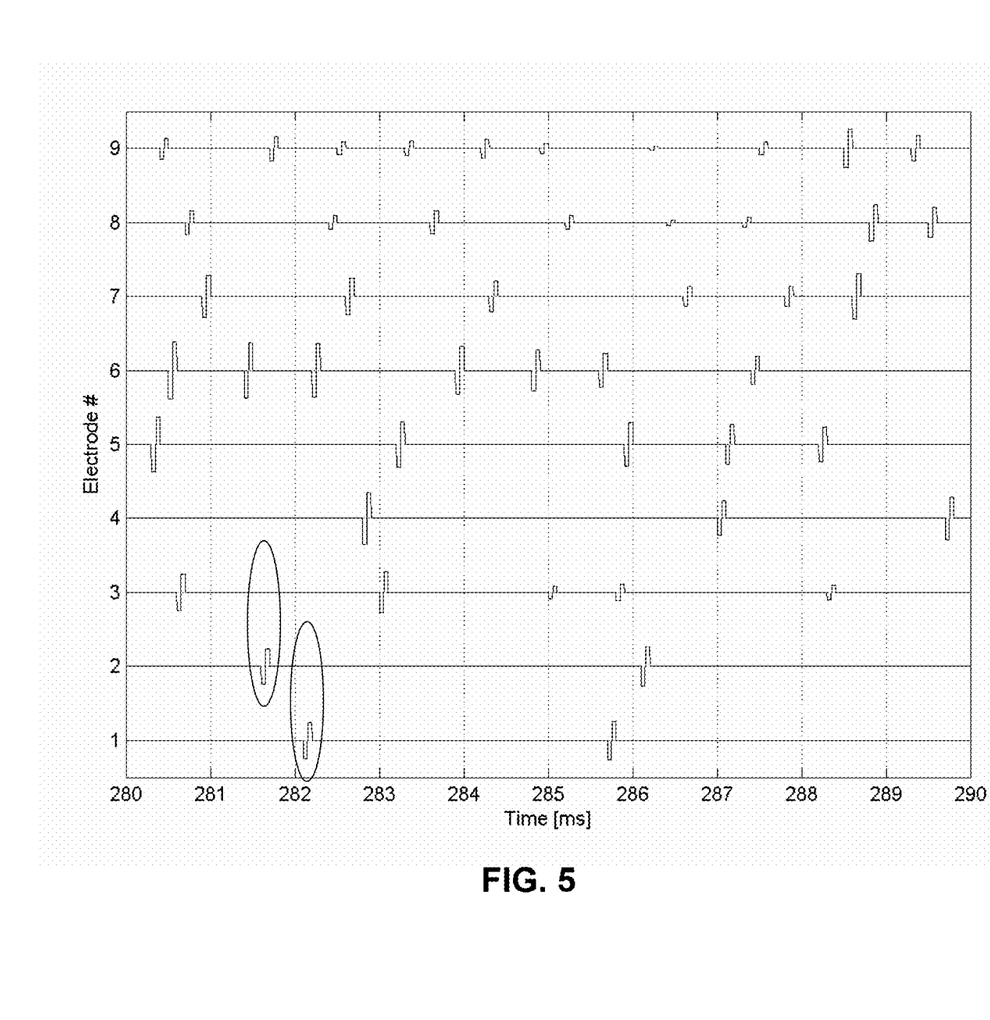
FIG. 5 illustrates a typical stimulation without weighting.
Figure 6:
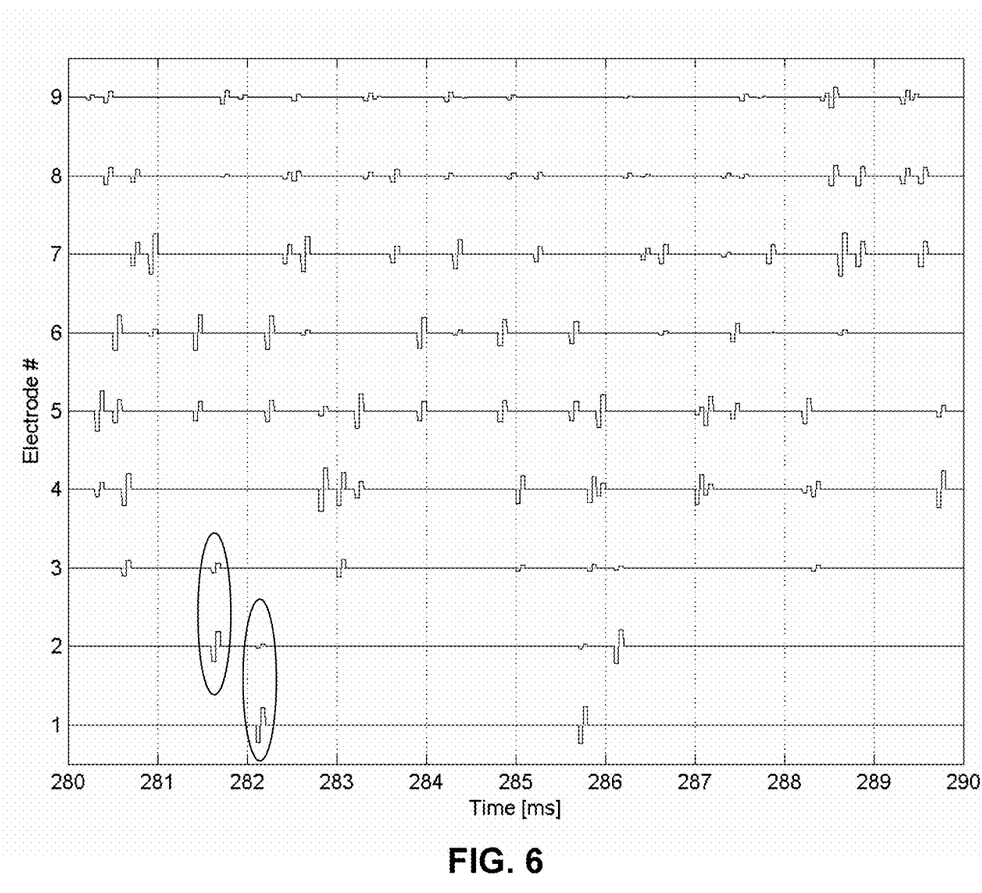
FIG. 6 illustrates a typical stimulation applying the weighting matrix.

In such an embodiment, Pulse Weighting 403 uses weighting-matrix W to determine a vector A such that the ILD and ITD are matched between the left and right CI system. FIG. 5 shows an example of typical output electrode pulses $E_1$ to $E_9$ for a unilateral system without weighting, while FIG. 6 shows the same output electrode pulses $E_1$ to $E_9$ processed and weighted by a typical embodiment as described above.

In other specific embodiments, a more complex and dynamic mapping function could take into account other signal characteristics of the stimulation event signals $S_1$ to $S_M$ such as signal levels and/or level changes. A level dependent behavior could be defined, for example, by a stack of matrices containing different weightings for different input levels of stimulation event signals $S_1$ to $S_M$. Various other different techniques could be used to determine the weighting matrix as a function of stimulation event signals $S_1$ to $S_M$ signal levels such as, for example, psychophysics, objective measures, and radiologic measures. Psychophysical methods could include ranking or scaling procedures as well as matching procedures. For example, the pitch perceived through electrical stimulation of single electrodes as well as weighted sums of electrode groups can be ranked across ears from low to high or scaled after pitch. Alternatively, single electrode stimuli on one side could get matched to weighted sums of simultaneous stimuli on the contralateral side by changing the weighting. Similarly, weighted sums of simultaneous stimuli on one side could get matched to weighted sums of simultaneous stimuli on the contralateral side by changing the weighting. Quality ratings and information transfer analysis of speech stimuli could be used to optimize the patient specific frequency-place map. In a specific embodiment, ITD and ILD discrimination could serve as a basis for the matching and weighting of interaural electrode groups. Objective measures could be used to determine the specific weighting, such as, for example, measurement of the electrical potentials evoked by weighted synchronous electrical stimulation of different intra-cochlear electrode groups across the two sides. Or radiologic methods like x-ray and computer tomography could be used to objectively determine electrode positions and calculate model based and bilaterally matched weighting functions for each side.

Figure 7:
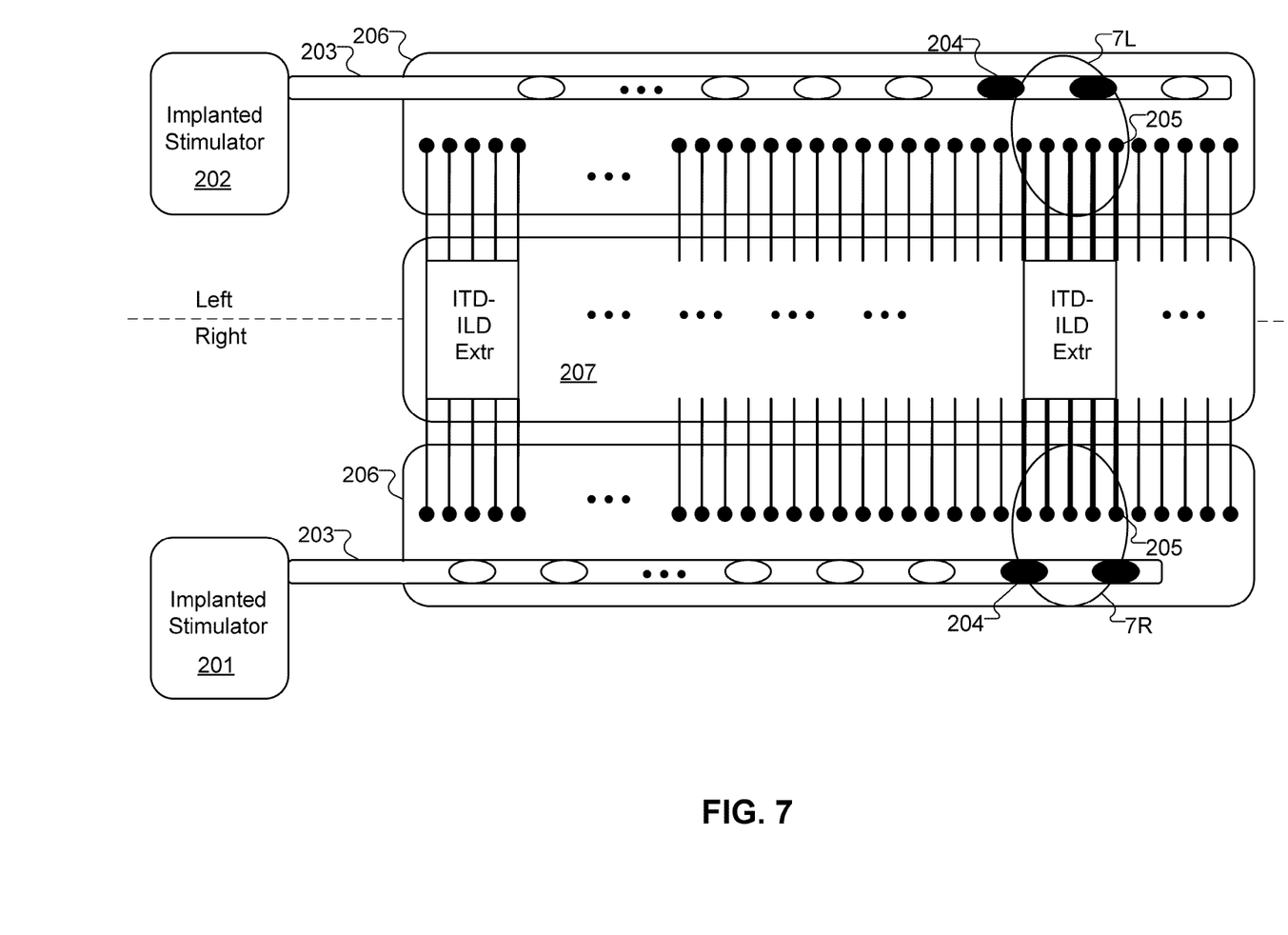
FIG. 7 illustrates the restoration of tonotopicity in a patient having interaurally mismatched electrode insertions by applying weighted stimulation.

Embodiments of the present invention avoid the problems discussed above with respect to prior CI systems and the coding of ITD information in the context of tonotopic mismatches. In a bilateral CI user, both sides can be pre-processed and filtered the same way using the same optimal filter bank on both sides. Thus, band specific ITDs and ILDs are carried within the stimulation event signals $S_1$ to $S_M$ and by weighting can be transmitted to interaurally matched nerve populations. FIG. 7 shows the effect of optimally adjusted bilateral weighting on the perception of ITDs and ILDs. In FIG. 7, the electrode array 203 and electrode contacts 204 are not in idealized alignment with respect to the corresponding neural tissue 205 on each side. But signal weighting optimizes the bilateral stimulation by the electrode contacts 204 for matched neural tissue 205—compare regions 7R and 7L.

A possible disadvantage of stimulating electrodes simultaneously as described above could be a higher power consumption. This aspect could be addressed in the selection of electrode groups (as described, for example, in US 2005203589 by Zierhofer, the contents of which are hereby incorporated herein by reference). A smaller number of electrodes stimulated simultaneously should be the result of a psychophysical or objective evaluation of stimulation groups. The aspect of power consumption of such a system could also be addressed by the Preprocessor Filter Bank 401 and/or Stimulation Pulse Generator 402 to reduce the number of stimulation events in a way that the relevant ITD and ILD information is still transmitted. The system described above combined with coding of the temporal fine structure would result in a reduction of the overall number of electrode stimulation pulses and would also stress low frequency ITD information conveyed in the binaural signals.

Figure 8:
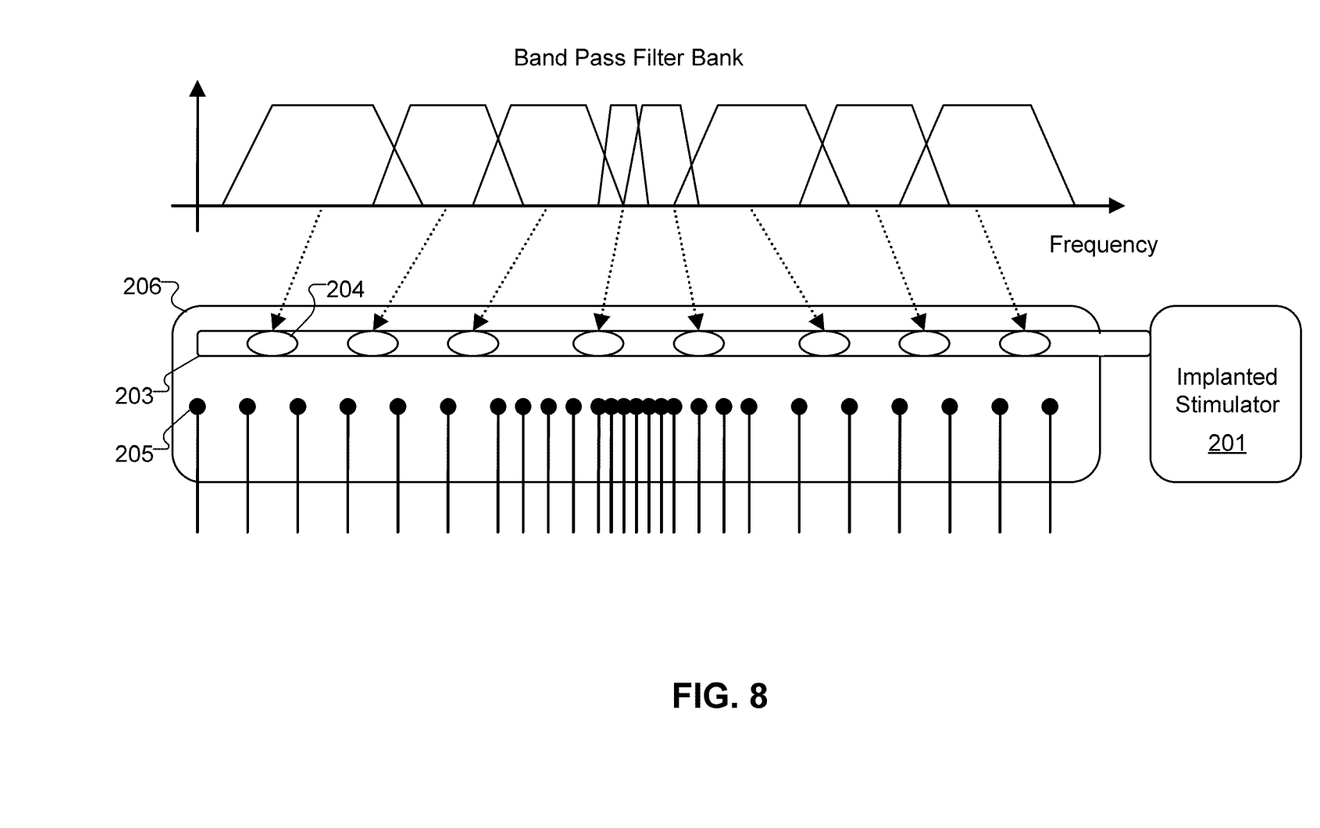
FIG. 8 illustrates a cochlear implant in a patient having different neuronal survival along the cochlea resulting in a distorted tonotopicity which is accounted for by a user-specific filter bank.
Figure 9:
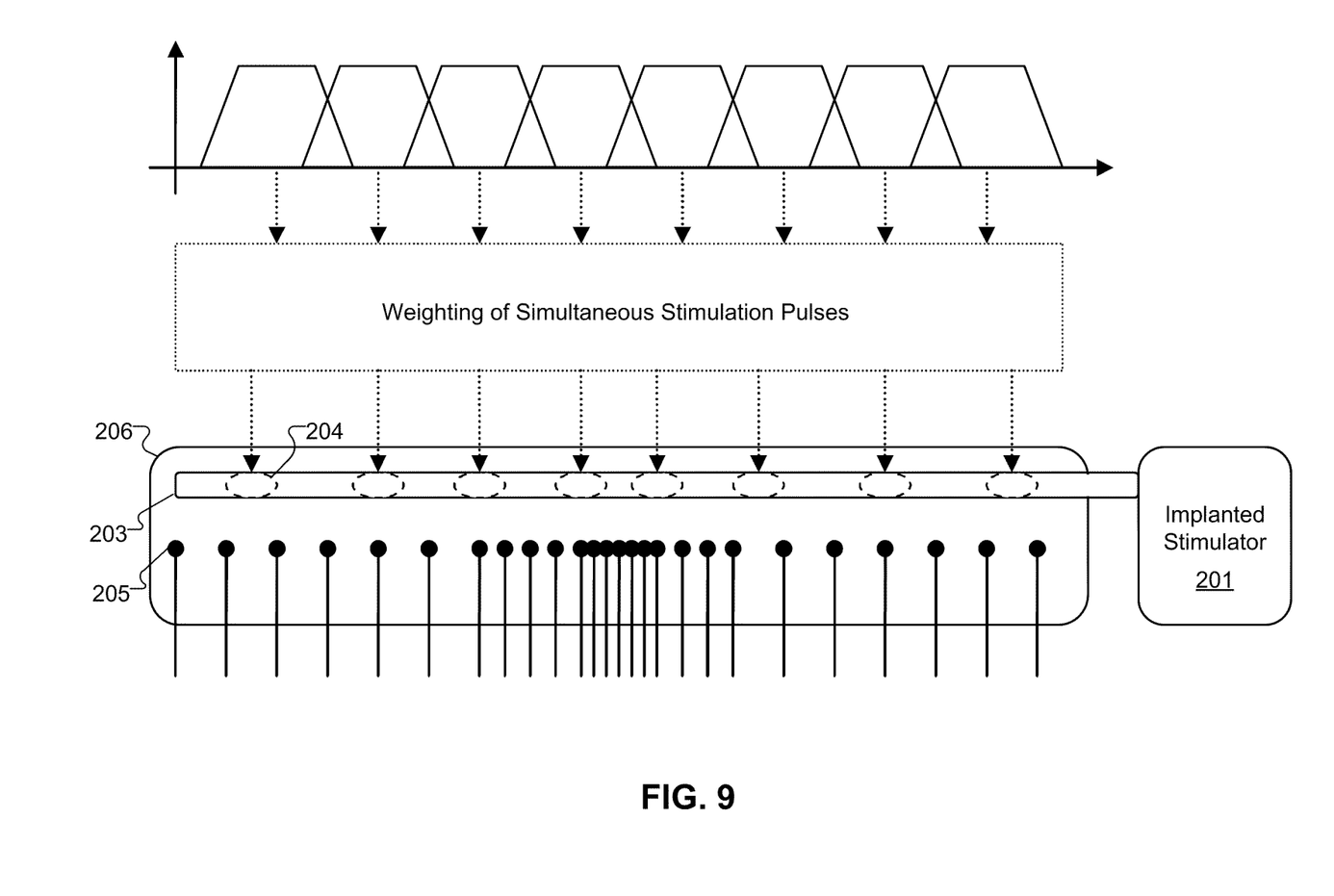
FIG. 9 illustrates a cochlear implant in a patient having different neuronal survival along the cochlea resulting in a distorted tonotopicity which is accounted for by weighted stimulation derived from an optimal filter bank.

In another specific embodiment, a weighting matrix could be used in a unilateral CI system to match an optimal analysis filter bank, i.e. physiologically based filters, to the patient specific electrode positions and neural survival within the cochlea and pitch perception. Without weighting, a tonotopically correct filter bank might be sub-optimal as depicted in FIG. 8 in a patient with non-homogenous nerve survival along the cochlea. In such a case, the above described weighting matrix system could be used to assign an optimal filter bank to a number of stimulation sites between two electrodes as shown in FIG. 9.

Embodiments of the invention may be implemented in any conventional computer programming language. For example, preferred embodiments may be implemented in a procedural programming language (e.g., "C") or an object oriented programming language (e.g. "C++", Python). Alternative embodiments of the invention may be implemented as pre-programmed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g. optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g. shrink wrapped software), preloaded with a computer system (e.g. on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g. a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of generating electrode stimulation signals for an implanted electrode array in a bilateral cochlear implant system with interaurally mismatched left and right side implanted electrode arrays, the method comprising:
   processing an acoustic audio signal input with a bank of filters, each filter being associated with a band of audio frequencies, to generate a set of band pass signals, each band pass signal corresponding to the band of frequencies associated with one of the filters and having a filter-associated group delay time;
   extracting stimulation information from the band pass signals to generate a set of stimulation event signals defining electrode stimulation signals;
   weighting the stimulation event signals based on a tonotopic approach using a weighted matrix of stimulation amplitudes reflecting patient-specific perceptual characteristics, interaural time delays (ITD), and the different filter-associated group delay times to produce a set of bilaterally optimized electrode stimulation signals with ITD directional information and restored tonotopicity to interaurally matched nerve populations; and
   developing the electrode stimulation signals into a set of output electrode pulses to electrode contacts in one of the interaurally mismatched electrode arrays.

2. A method according to claim 1, wherein the stimulation information includes at least one of envelope information, phase information, and timing of electrode stimulation signals.

3. A method according to claim 1, wherein the electrode stimulation signals are simultaneous signals.

4. A method according to claim 1, wherein the band pass signals form a multi-dimensional vector.

5. A method according to claim 1, wherein the perceptual characteristics include signal levels in the band pass signals.

6. A method according to claim 1, wherein the perceptual characteristics are defined according to a psychophysical method.

7. A method according to claim 6, wherein the psychophysical method includes at least one of a ranking procedure and a scaling procedure.

8. A method according to claim 6, wherein the psychophysical method includes a matching procedure.

9. A method according to claim 8, wherein the matching procedure includes matching a single electrode stimulus on one of the pair of electrode arrays to a weighted sum of simultaneous electrode stimuli on the contralateral side.

10. A method according to claim 1, wherein the perceptual characteristics are based on patient-specific objective measurements.

11. A method according to claim 10, wherein the objective measurements include measurement of electrical potentials evoked by weighted synchronous electrical stimulation of electrodes in the implanted electrode array.

12. A method according to claim 10 wherein the objective measurements include imaging measurement of electrode position in the implanted electrode array.

13. A method according to claim 1, wherein the patient-specific perceptual characteristics include interaural level differences (ILD).

14. A bilateral cochlear implant system with interaurally mismatched left and right side implanted electrode arrays, the system comprising:
- a preprocessor including a bank of filters, each filter being associated with a band of audio frequencies, for processing an acoustic audio signal input to generate a set of band pass signals, each band pass signal corresponding to the band of frequencies associated with one of the filters and having a filter-associated group delay time;
- a stimulation pulse generator for extracting stimulation information from the band pass signals to generate a set of stimulation event signals defining electrode stimulation signals;
- a pulse weighting module for weighting the stimulation event signals based on a tonotopic approach using a weighted matrix of stimulation amplitudes reflecting patient-specific perceptual characteristics, interaural time delays (ITD), and the different filter-associated group delay times to produce a set of electrode stimulation signals with ITD directional information and restored tonotopicity to interaurally matched nerve populations; and
- a pulse shaper for developing the electrode stimulation signals into a set of output electrode pulses to electrode contacts in one of the interaurally mismatched electrode arrays.

15. A system according to claim 14, wherein the stimulation pulse generator extracts stimulation information that includes at least one of envelope information, phase information, and timing of electrode stimulation signals.

16. A system according to claim 14, wherein the pulse shaper develops simultaneous electrode stimulation signals.

17. A system according to claim 14, wherein the preprocessor generates a multi-dimensional vector to represent the set of band pass signals.

18. A system according to claim 14, wherein the perceptual characteristics include signal levels in the band pass signals.

19. A system according to claim 14, wherein the perceptual characteristics are defined according to a psychophysical system.

20. A system according to claim 19, wherein the psychophysical system includes at least one of a ranking procedure and a scaling procedure.

21. A system according to claim 19, wherein the psychophysical system includes a matching procedure.

22. A system according to claim 21, wherein the matching procedure includes matching a single electrode stimulus on one of the pair of electrode arrays to a weighted sum of simultaneous electrode stimuli on the contralateral side.

23. A system according to claim 14, wherein the perceptual characteristics are based on patient-specific objective measurements.

24. A system according to claim 23, wherein the objective measurements include measurement of electrical potentials evoked by weighted synchronous electrical stimulation of electrodes in the implanted electrode array.

25. A system according to claim 23, wherein the objective measurements include imaging measurement of electrode position in the implanted electrode array.

26. A system according to claim 14, wherein the patient-specific perceptual characteristics include interaural level differences (ILD).

* * * * *